(12) United States Patent
Berner et al.

(10) Patent No.: US 9,101,465 B2
(45) Date of Patent: Aug. 11, 2015

(54) APPLICATOR FOR INSERTING LENSES

(75) Inventors: Werner Berner, Erlinsbach (CH); Thomas Hauri, Staffelbach (CH)

(73) Assignee: Neoptics AG, Hunenberg (CH)

( * ) Notice: Subject to any disclaimer, the term of this patent is extended or adjusted under 35 U.S.C. 154(b) by 203 days.

(21) Appl. No.: 13/513,275

(22) PCT Filed: Dec. 3, 2010

(86) PCT No.: PCT/EP2010/068841
§ 371 (c)(1),
(2), (4) Date: Jun. 1, 2012

(87) PCT Pub. No.: WO2011/069907
PCT Pub. Date: Jun. 16, 2011

(65) Prior Publication Data
US 2012/0245592 A1    Sep. 27, 2012

(30) Foreign Application Priority Data

Dec. 9, 2009  (EP) .................................... 09178484

(51) Int. Cl.
*A61F 2/16* (2006.01)
*A61F 2/14* (2006.01)
*A61F 2/00* (2006.01)

(52) U.S. Cl.
CPC ............... *A61F 2/146* (2013.01); *A61F 2/0095* (2013.01); *A61F 2/148* (2013.01); *A61F 2/1678* (2013.01)

(58) Field of Classification Search
CPC .............................. A61F 2/1662; A61F 9/0026
USPC ........................................ 623/6.12; 606/107
See application file for complete search history.

(56) References Cited

U.S. PATENT DOCUMENTS

| | | | | |
|---|---|---|---|---|
| 4,257,406 A | * | 3/1981 | Schenk | 600/219 |
| 4,836,201 A | | 6/1989 | Patton et al. | |
| 5,066,297 A | * | 11/1991 | Cumming | 606/107 |
| 5,100,410 A | * | 3/1992 | Dulebohn | 606/107 |
| 5,123,905 A | * | 6/1992 | Kelman | 606/107 |
| 5,217,464 A | * | 6/1993 | McDonald | 606/107 |
| 5,242,450 A | * | 9/1993 | McDonald | 606/107 |
| 5,776,138 A | | 7/1998 | Vidal et al. | |
| RE37,387 E | * | 9/2001 | Brady et al. | 606/107 |
| 6,497,708 B1 | * | 12/2002 | Cumming | 606/107 |
| 6,605,093 B1 | * | 8/2003 | Blake | 606/107 |

(Continued)

FOREIGN PATENT DOCUMENTS

| | | |
|---|---|---|
| JP | 2000513955 A | 10/2000 |
| JP | 2008513044 A | 5/2008 |

(Continued)

*Primary Examiner* — Tuan V Nguyen
*Assistant Examiner* — Chima Igboko
(74) *Attorney, Agent, or Firm* — Davis & Bujold, P.L.L.C.; Michael J. Bujold (57) ABSTRACT

A pre-load unit, for inserting a lens into the eye of a human or animal, includes a housing, a lens-receiving part arranged on or in the housing, having a section that protrudes from the housing, and two separate leaf-like units which, at least at their ends directed away from the housing, are in releasable contact with each other and form a chamber of storing an optical lens. A slide which is arranged movably in the interior of the housing can be moved between the leaf-like units of the lens-receiving unit. The pre-load unit may be combined with a grip piece, wherein the pre-load unit and the grip piece are connected to each other in such a way that the pre-load unit can be moved inside the grip piece.

18 Claims, 7 Drawing Sheets

(56) References Cited

U.S. PATENT DOCUMENTS

| | | | |
|---|---|---|---|
| 6,976,989 B1* | 12/2005 | Vincent | 606/107 |
| 8,470,029 B2* | 6/2013 | Walter et al. | 623/6.12 |
| 2002/0022881 A1* | 2/2002 | Figueroa et al. | 623/6.12 |
| 2004/0215207 A1* | 10/2004 | Cumming | 606/107 |
| 2005/0283163 A1* | 12/2005 | Portney et al. | 606/107 |
| 2006/0004381 A1* | 1/2006 | Feingold et al. | 606/107 |
| 2007/0244559 A1* | 10/2007 | Shiuey | 623/5.11 |
| 2007/0250068 A1* | 10/2007 | Vincent-Aubry | 606/107 |
| 2008/0033449 A1* | 2/2008 | Cole et al. | 606/107 |
| 2008/0119865 A1* | 5/2008 | Meunier et al. | 606/107 |
| 2008/0154361 A1* | 6/2008 | Pynson et al. | 623/6.12 |
| 2008/0243138 A1* | 10/2008 | Dishler et al. | 606/107 |
| 2008/0275462 A1* | 11/2008 | Feingold et al. | 606/107 |
| 2009/0112313 A1* | 4/2009 | Mentak | 623/6.12 |

FOREIGN PATENT DOCUMENTS

| | | |
|---|---|---|
| WO | 2006/007543 | 1/2000 |
| WO | 2009/010751 | 1/2009 |
| WO | 2009/075685 | 6/2009 |

* cited by examiner

APPLICATOR FOR INSERTING LENSES

The present invention relates to an applicator for inserting optical lenses into the eye of a human or animal.

In various procedures for improving the visual acuity of the human eye, it is customary to insert an optical lens into the eye. For example, corrective lenses are introduced into a pocket that has been created beforehand in the cornea (for example by means of a laser or a keratome). The lenses are inserted into these pockets using a lens insertion device (applicator).

The applicators known from the prior art function in such a way that a lens held by the applicator is ejected from the applicator into the corneal pocket. Applicators of this kind are disclosed, for example, in WO 2006/007543 and in U.S. Pat. No. 5,123,905.

The ejected lenses first have to partially deploy in the pocket and, moreover, still generally have to be positioned with precision in the pocket. The lenses used are very flexible and are difficult to handle.

There was therefore a need for an applicator with which optical lenses can be introduced into the eye of a human or animal more easily and more exactly.

The above object is achieved by the applicator according to the invention.

The present invention is based on an entirely different principle for inserting a lens into the eye. Instead of ejecting the lens into the interior of the eye with the aid of a customary applicator as in the prior art, the applicator according to the invention ensures that the lens is already correctly positioned in the eye while still located inside the applicator. With the position of the lens being maintained, the applicator is then withdrawn by a distance defined by the grip piece, and the lens is thus released at the correct position. The applicator is then withdrawn from the corneal pocket.

This permits much easier and more exact positioning of the lens at the desired location in the eye. Instead of positioning the flexible and difficult-to-handle lens after it has been ejected into the eye, the more easily handled applicator is exactly oriented. The applicator is then removed, while the lens remains positioned in situ.

This is achieved by a two-part design of the applicator according to the invention. The applicator according to the invention comprises a pre-load unit, which can be fitted with a lens, and a grip piece. Pre-load unit and grip piece can be connected to each other in such a way that the pre-load unit can be drawn back by a defined distance and the slide remains in position. This is achieved by first fixing the lens with the aid of a slide, which is movable independently of the rest of the pre-load unit. The pre-load unit is preferably designed with an anti-rotation means, such that the orientation of the lens is maintained even after attachment to the grip piece.

According to the present invention, withdrawal by a defined distance is understood as meaning that the corresponding structural part can be drawn into the grip piece along a defined length. The length is in this case defined by the nature of the grip piece but must be at least such that the lens contained in the pre-load unit can be released from the pre-load unit.

One aspect of the present invention concerns a pre-load unit for inserting lenses into the eye of a human or animal, comprising i) a housing with means for fastening the unit to a grip piece, preferably in a manner secure against rotation, ii) a lens-receiving part arranged on or in the housing and comprising a section that protrudes from the housing and that has two separate leaf-like units which, at least at their ends directed away from the housing, are in releasable contact with each other and there form a chamber for storing an optical lens, iii) a slide, which is arranged movably in the interior of the housing and can be moved between the leaf-like units of the lens-receiving unit.

According to the present invention, a leaf-like unit is to be understood as a structural part which is very thin, similarly to a leaf, and thus has corresponding flexibility. According to the present invention, the leaf-like units typically have a thickness of between 0.1 and 0.3 mm and typically have a length of 20-40 mm, preferably 20 to 30 mm.

According to a preferred embodiment, the two leaf-like units each have at least one hole, preferably exactly one hole, and the holes are arranged such that they lie directly over each other and form an opening through the center of the chamber for storing an optical lens. In this way, a lens located in the chamber can be positioned particularly easily on the visual axis of the eye. The person inserting the lens sees the lens through the opening and can align it exactly. These holes can typically have a diameter of 0.3 to 0.6 mm. This embodiment is particularly advantageous for intracorneal lenses with a central hole, as are described in WO 2009/075685.

The present invention, according to its particularly preferred embodiment, comprises a pre-load unit with precisely two leaf-like units of this kind. However, it is also possible to use pre-load units with more than two leaf-like units, for example four leaf-like units, and the leaf-like units together form a chamber for storing an optical lens.

As has been described above, the leaf-like units of the lens-receiving part, at their ends directed away from the housing, form a chamber for storing an optical lens. This chamber must be able to be opened in order to insert the lens into the chamber or to remove the lens again from the chamber. According to the present invention, the leaf-like units are therefore in loose contact with each other in the area of the chamber, i.e. they can be moved apart from each other by application of force. For example, the leaf-like units can be spread apart from each other by means of the slide described in more detail below. However, to cancel the contact between the leaf-like units, such a force needs to be applied.

In order to hold the lens in place inside the chamber, the chamber is at least partially bounded by wave-shaped sections, which are present on both leaf-like units and are arranged such that the sections of one leaf-like unit mesh with the corresponding sections of the other leaf-like unit. In this way, a chamber is formed which is, as it were, "grated". Particularly preferably, these boundaries form a chamber into which it is possible to introduce the lens that is to be inserted into the eye.

According to the invention, these boundaries are preferably arranged on the leaf-like units in such a way that, in the state of contact between the two leaf-like units, the lens cannot slip out of the chamber and it is movable in the chamber (for example by means of the boundaries being provided at all corners of the chamber). Preferably, the wave-shaped sections are also slightly raised.

As has been stated above, the fundamentally novel principle of the present invention is that the lens is not ejected into a corneal pocket, and instead the applicator is positioned exactly in the corneal pocket and then, with the lens maintained in position, the leaf-like parts are drawn back by an exactly defined distance. Therefore, the section of the applicator (or of the pre-load unit of the applicator) in which the chamber for storing an optical lens is formed must be configured in such a way that it can be inserted into a corresponding corneal pocket. According to the invention, the shape of the area of the applicator forming this chamber preferably corresponds substantially to the shape of the lens to be inserted, or it is even slightly smaller in width than the corresponding lens. This is possible, for example, by the chamber not having a round shape and not having the above-described boundaries all around, i.e. the chamber is laterally open between the boundaries. The lens located in the chamber can then protrude from the chamber at some points.

According to the invention, the leaf-like units of the pre-load unit, in the area of the chamber, preferably have a width of 3 mm or slightly less. However, this can vary depending on the lens that is to be put in place.

To allow the chamber to be opened, the leaf-like units must be able to be spread apart from each other. They must therefore be made of a sufficiently flexible material. According to the present invention, the material used for the leaf-like units is a physiologically compatible plastic or a physiologically compatible metal.

The leaf-like units typically have a length of 20 to 40 mm, preferably 20 to 30 mm. They preferably merge, with increasing thickness, into a section of the lens-receiving part arranged fixedly in the housing of the pre-load unit. Alternatively, however, the leaf-like units can also have a constant thickness and can be fastened to a section of the lens-receiving part arranged fixedly in the housing of the pre-load unit. In any case, however, there is a sufficiently large gap between the leaf-like units to ensure that the slide explained below can be moved freely therein. Moreover, the leaf-like units are in any case fastened to the wider section of the lens-receiving part, or even directly to the housing, in such a way that they touch each other at their ends directed away from the housing and there form the above-described chamber.

The housing of the pre-load unit serves to fix the lens-receiving unit. According to the invention, the lens-receiving unit is preferably guided into the housing and is locked there by suitable anchoring mechanisms. Alternatively, however, the lens-receiving unit can also be arranged fixedly on the housing, for example.

The housing of the pre-load unit has a continuous bore, in which the slide explained in more detail below can move freely.

The pre-load unit is provided for use in an applicator according to the invention. For this purpose, the housing of the pre-load unit has means for fastening the unit to a grip piece. These means are arranged at the end of the housing directed away from the end with the protruding leaf-like units. The connection to the grip piece is preferably such that it can only be made in a manner secure against rotation.

According to the invention, the fastening means are preferably means for producing a bayonet connection to the grip piece. However, other suitable fastening means can of course also be used.

As has been explained above, the principle according to the invention is that, after the positioning in the corneal pocket has been carried out, the pre-load unit is drawn back by a defined distance while the lens is maintained in place. For this purpose, the pre-load unit must be movable into the grip piece. This is explained in more detail below. According to the invention, however, the pre-load unit preferably has a stop for limiting the movement of the pre-load unit into the grip piece. This stop can, for example, be an elevation on an area of the surface of the housing. Preferably, this elevation is designed in a ring shape around the entire circumference of the housing. The stop is arranged at a place on the housing of the pre-load unit such that the housing can be moved into the grip piece to such an extent that the leaf-like units no longer cover the lens located in the chamber, i.e. the lens is exposed.

According to the invention, the pre-load unit is designed for one-off use. The pre-load unit is accordingly fitted with a corresponding lens and then placed in a sterile package and, shortly before the insertion procedure, is recovered from the package and connected to the grip piece.

To fit the pre-load unit with a lens, the leaf-like units are spread apart from each other in order to permit access to the above-described chamber. According to one embodiment of the present invention, this can be done by inserting a suitable tool, for example a knife, into the lateral gap between the leaf-like units. The lens is then placed in the accessible chamber, preferably under a microscope. The tool is then removed from the lateral gap between the leaf-like units, as a result of which the leaf-like units again come into contact with each other at their ends and the chamber is closed. For the loading procedure, it is possible, for example, to provide a loading station in which the pre-load unit can be fixed. The loading station has a rotatable tool (e.g. a knife), which can be rotated into the lateral gap between the leaf-like units and rotated back out of said gap.

According to the invention, at least one leaf-like unit preferably has a further hole, which is arranged above the boundary of the chamber for storing an optical lens. In the above-mentioned loading procedure, this permits better monitoring of the correct placement of the lens in the chamber, since the person performing the procedure can see through the hole that the lens is arranged exactly in the chamber and does not lie, for example, on one of the boundaries. This second hole can typically have a diameter of 0.3 to 0.6 mm.

An essential element of the pre-load unit according to the invention is a slide, which is arranged movably in the interior of the housing and can be moved between the leaf-like units of the lens-receiving unit. This slide must be able to be moved forward between the leaf-like units to such an extent that it comes into contact with the lens located in the chamber and can fix this lens. The slide preferably tapers toward the end that is to move between the leaf-like units. To better fix the lens, the front end of the slide is correspondingly designed to complement the lens shape.

Inside the housing, the slide is movable freely and independently of the other structural parts. Preferably, the section of the slide located in the housing of the pre-load unit has a thickness of just less than the diameter of the continuous bore in the housing of the pre-load unit. Inside this bore, the slide can be accessed by control elements of the grip piece described below.

As has been mentioned above, the pre-load unit is preferably designed for one-off use. Therefore, according to a further aspect of the present invention, the pre-load unit is stored in a sterile package, from which it is only removed, and connected to the grip piece, directly before the insertion of the lens into the eye.

The present invention thus also relates to a kit comprising a storage unit and an above-described pre-load unit in the interior of the storage unit, wherein the storage unit is made of a watertight material and can be closed in a watertight manner with a stopper.

Particularly preferably, the pre-load unit is fitted with the desired optical lens and then placed in a sterile package. This facilitates the work of the person inserting the lens.

To be able to store the pre-load unit in a sterile state over a long period of time, it is packaged in a storage unit that protects the pre-load unit from environmental influences. For this purpose, the interior of the storage unit is filled with a storage liquid, which constantly covers at least the lens located in the chamber of the pre-load unit. This storage liquid can be water. However, the storage liquid is preferably physiological saline (NaCl).

The storage unit is made from a material that is watertight and therefore also allows only very little water vapor, if any, to pass through. This is important in order to ensure a sufficient level of storage liquid within the storage unit during the entire storage period. If the material were not watertight, the storage liquid would evaporate over a certain time, and the lens in the chamber of the pre-load unit would no longer be stored in a sterile state. Watertight materials are known to those skilled in the art. Examples of such a material are glass or a watertight plastic. After introduction of the pre-load unit, the storage unit is closed in a watertight manner by means of a suitable stopper. This stopper is preferably made from a watertight plastic.

The applicator according to the invention furthermore comprises a grip piece. This is typically an elongate tube with a shape that ensures the grip piece can be easily held in the hand. As has been mentioned above, the grip piece is designed at one end in such a way that the pre-load unit and the grip piece can be connected to each other such that the pre-load unit can be moved inside the grip piece. For this purpose, the grip piece has a diameter exceeding the diameter of the part of the pre-load unit that is to be inserted into the grip piece. The grip piece is hollow on the inside, at least at the end to be connected to the pre-load unit. However, it is preferably a completely hollow tube.

The pre-load unit is connected to parts inside the grip piece that are movable. Thus, by means of a movement of these parts, the pre-load unit is also moved. This movement is preferably effected with the aid of a control element located on the surface of the grip piece. The control element is preferably a slide which, by way of an elongate opening in the grip piece, is connected to the corresponding parts in the interior of the grip piece.

According to the present invention, the slide of the pre-load unit is to be moved independently of the rest of the pre-load unit. According to the invention, this is preferably achieved by a further control element, which is likewise located on the surface of the grip piece. This control element is preferably also a slide which, by way of an elongate opening in the grip piece, is connected to corresponding insert parts in the interior of the grip piece. These insert parts are akin to the ejector of a gun. When the control element on the surface of the grip piece is moved forward, the insert parts come into contact with the slide of the pre-load unit and move the slide forward independently of the rest of the pre-load unit.

According to a preferred embodiment of the present invention, in order to fix these insert parts in the grip piece, a pin mounted on the insert parts protrudes through an opening in the grip piece and is fixed there.

According to a particularly preferred embodiment of the present invention, the two control elements described above are connected to each other in such a way that the second control element, which moves the pre-load unit except for the slide, can only be operated when the first control element, which moves the slide of the pre-load unit, is located in a position in which the slide moved by it is driven out to the maximum extent from the housing of the pre-load unit. Otherwise, the second control element is locked. This prevents inadvertent movement of the leaf-like units of the pre-load unit without the lens first having been fixed in position.

According to an alternative embodiment of the present invention, the grip piece can have just one control element. In this embodiment, the one control element is used to move the slide of the pre-load unit. The control element is located on the surface of the grip piece. This control element is also preferably a slide which, by way of an elongate opening in the grip piece, is connected to corresponding insert parts in the interior of the grip piece. These insert parts are akin to the ejector of a gun. If the control element on the surface of the grip piece is moved forward, the insert parts come into contact with the slide of the pre-load unit and move the slide forward independently of the rest of the pre-load unit. The particular aspect of this embodiment is that the maximum forward movement of the slide by the control element releases a locking mechanism, as a result of which the rest of the pre-load unit, with the leaf-like units arranged thereon, becomes movable. The release of the locking mechanism preferably brings about an automatic movement of the rest of the pre-load unit, with the leaf-like units arranged thereon, into the grip piece, for example via a spring mechanism. In this way, release of the lens is achieved through the maximum forward movement of the single control element.

The grip piece of the applicator according to the invention is intended to be used more than once. For this purpose, according to a preferred embodiment of the present invention, the grip piece can be completely dismantled, such that all the structural parts can be completely cleaned and sterilized. According to this embodiment, the control elements arranged on the surface can be removed, as a result of which the structural parts in the interior of the grip piece that are connected to the control elements can be withdrawn from the grip piece. In the case of the insert parts provided for moving the slide, the above-described pin additionally has to be pressed out of the opening so as to be able to remove the insert parts.

After cleaning has been carried out, the grip piece can be reassembled, with care being taken to ensure that the control elements are located in the correct position.

However, according to an alternative embodiment of the present invention, the grip piece can also be provided for one-off use. Accordingly, in this embodiment, it is not necessary for the grip piece to be able to be dismantled for cleaning purposes. According to this embodiment, the grip piece is preferably stored separately until use, likewise in a storage unit analogously to the above-described unit. However, according to this embodiment, it is also conceivable that the pre-load unit and the grip piece are already stored as a unit until use (either separately, as described above, or also fixedly connected to each other), in a storage unit analogously to the above-described unit. According to this alternative embodiment, the applicator can therefore be constructed differently in that the parts for connecting grip piece and pre-load unit can be replaced by a fixed connection of these structural parts.

The applicator according to the invention permits easier and more exact positioning of a lens in the eye. This preferably entails the correct positioning of an intracorneal lens in a corneal pocket.

According to a further aspect, the present invention also relates to a method for inserting an optical lens, preferably an intracorneal lens, into the eye of a human or animal, comprising the steps of a) positioning the above-described applicator at the desired location of the eye, preferably in a pocket in the human cornea, such that the center of the optical lens contained in the applicator lies on the visual axis of the eye;

b) pushing the slide forward by means of a first control element on the grip piece, until the slide comes into contact with the lens without moving the latter, wherein at the same time the leaf-like units of the lens-receiving part are spread apart from each other;

c) withdrawing the rest of the pre-load unit by a defined distance by means of a second control element on the grip piece, with simultaneous fixing of the slide, as a result of which the lens is released from the applicator.

The pre-load unit, preferably stored in a sterile state, is removed from the storage container and connected to the grip piece, preferably in a manner secure against rotation. The applicator thus obtained, fitted with the lens, is then positioned at the desired location of the eye. Preferably, the ends of the leaf-like units of the pre-load unit which form the chamber, with the lens located therein, are inserted into a pocket that has been created beforehand in the cornea of an eye. According to a particularly preferred embodiment of the present invention, the pre-load unit has an opening extending through the chamber with the lens. This allows the person performing the procedure to align the lens exactly on the visual axis of the eye while the lens is still located in the chamber of the applicator. This can be done much more easily according to the invention, since the applicator is much easier to handle than a single, small and flexible lens.

The lens is then fixed inside the applicator by means of the first control element on the grip piece being pushed fully forward, as a result of which the slide of the pre-load unit is moved forward to the maximum extent, such that it comes into contact with the lens located in the chamber. This is made possible by the fact that, as a result of the forward movement of the slide, the leaf-like units are spread apart from each other and the interior of the chamber thus becomes accessible.

In the next step, the rest of the pre-load unit, except for the slide, is drawn back from the eye by a defined distance with the aid of the second control element, with the rest of the pre-load unit being drawn into the grip piece. During this step, the slide remains fixed and thus holds the lens exactly at the previously aligned position.

By means of the rest of the pre-load unit being drawn back, the lens is released from the applicator exactly in the previously aligned position. The lens is thus already placed in the eye as desired. According to the present invention, a further aligning step is no longer required.

The applicator is then removed from the eye and dismantled into its individual parts. The pre-load unit intended for one-off use is now preferably disposed of, while the grip piece is dismantled and cleaned, such that it is available for the next use with a new pre-load unit.

The present invention is intended above all for the insertion of optical lenses, in particular intracorneal lenses into corneal pockets. In principle, however, the applicator according to the invention can also be used to insert articles other than lenses into the eye.

An example that may be mentioned is the insertion of tissue ("donor cornea") in DSAEK (DESCEMET STRIPPING AUTOMATED ENDOTHELIAL KERATOPLASTY). This technique is used when the endothelium (of the posterior surface of the cornea) is damaged, so as to treat corneal blindness caused by this damage (review in Cursiefen/Kruse, Ophthalmologe 2008, 105, 183-192).

An advantage of the DSAEK technique is that only the diseased corneal layer is replaced, not the entire cornea. A keratome (as described in EP 1 778 141 A1, for example) is used to make a small incision in the outer layer of the cornea. The cornea is then exposed, and the region that has become opaque is replaced by donor cornea.

The layer of donor cornea can be inserted here with the aid of the applicator according to the invention. Instead of a lens, the chamber of the pre-load unit in this variant contains a donor cornea, which can be placed in the corneal pocket in a manner analogous to that described above for a lens. In principle, no further adaptations of the applicator or of the procedure performed with the applicator are needed.

The present invention is explained in more detail below with reference to non-limiting figures and examples.

Figure 1:
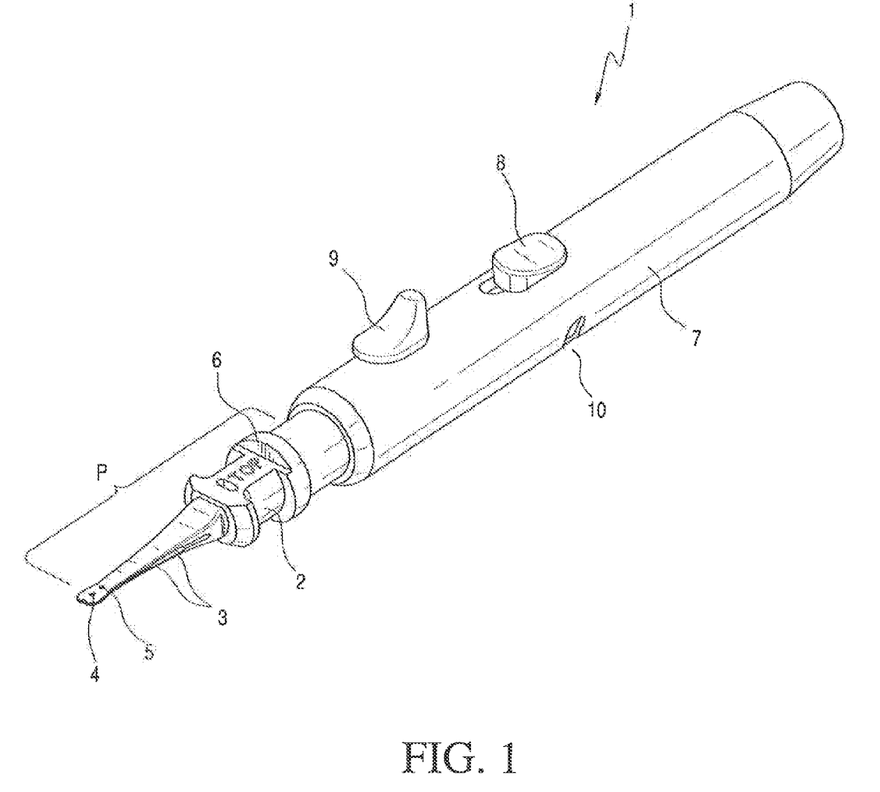
FIG. 1 shows an embodiment of the applicator according to the invention.

FIG. 1 shows an embodiment of the applicator 1 according to the invention. A pre-load unit P is mounted movably in the grip piece 7. The pre-load unit P comprises a housing 2, two leaf-like units 3 and a stop 6. In the leaf-like units 3, a continuous opening 4 is present through the center of the chamber (not shown here) for receiving a lens. A further hole 5, which makes it easier to fit the applicator 1 with a lens is additionally provided. Two control elements 8 and 9 are mounted on the grip piece 7. A pin, protruding from the lateral opening 10, is fastened to the insert parts present in the grip piece and fixes these parts in the grip piece 7.

Figure 2:
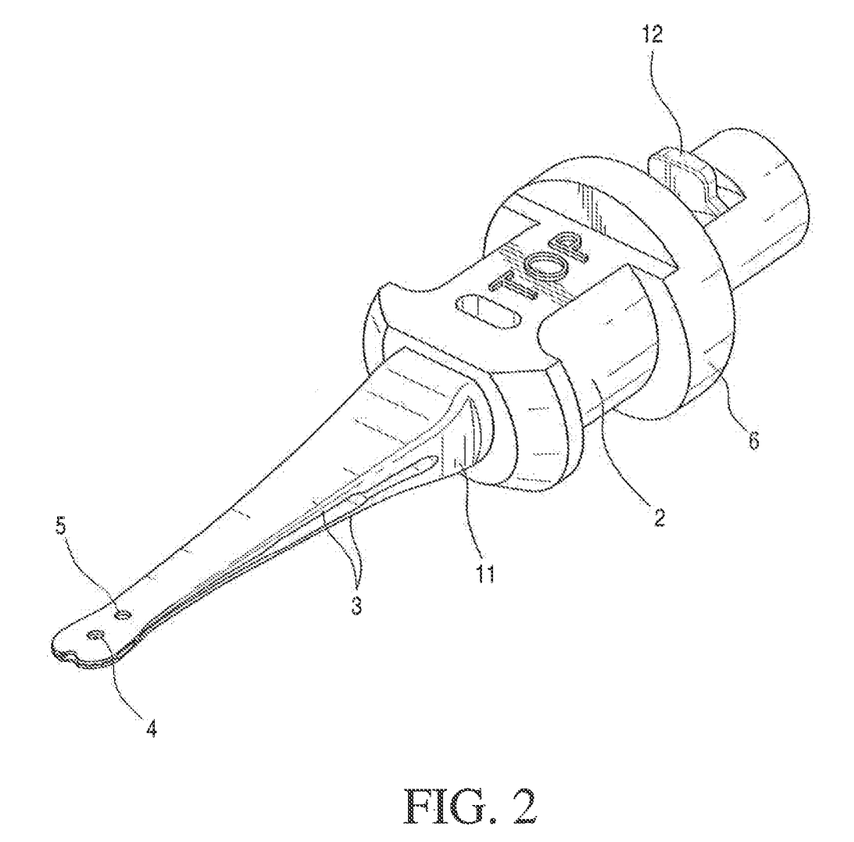
FIG. 2 shows an embodiment of the pre-load unit according to the invention.

FIG. 2 shows the pre-load unit P from FIG. 1 separately and in more detail. The lens-receiving part 11 is locked in the housing 2. The lens-receiving part 11 protrudes from the housing 2 and merges into the two leaf-like units 3. Fastening means 12 for connecting the pre-load unit P to the grip piece 7 are located at the other end of the housing 2. In the present case, a bayonet connection is formed.

Figure 3A:
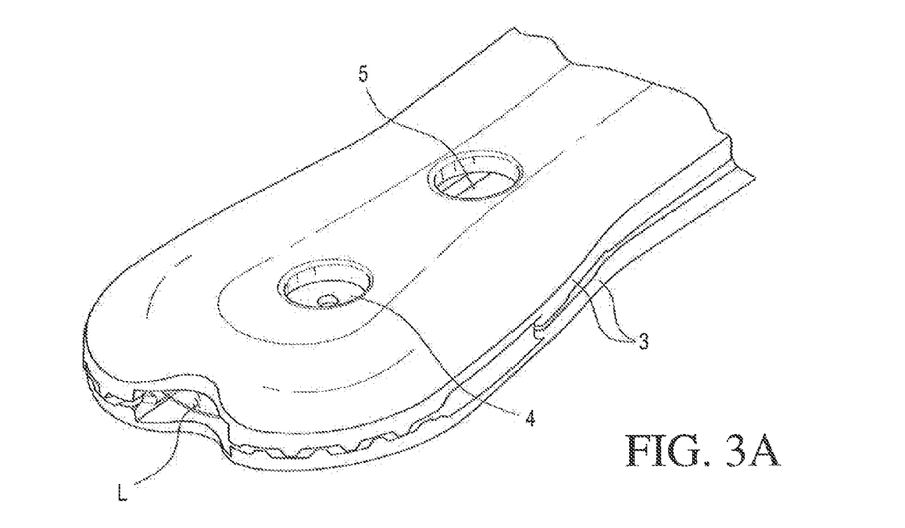
FIG. 3a shows an embodiment of the front section of the pre-load unit according to the invention.
Figure 3B:
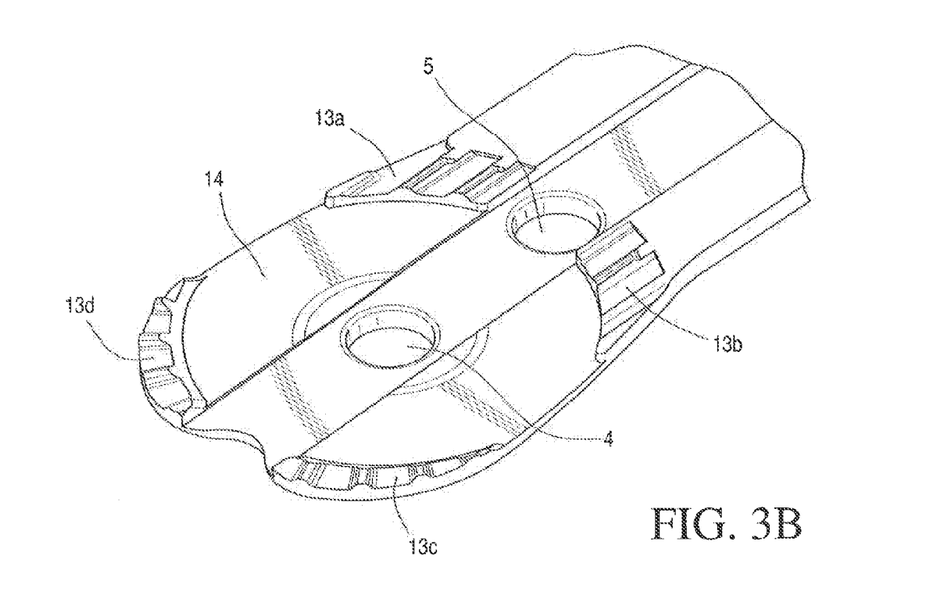
FIG. 3b shows the front section of the pre-load unit according to the invention from FIG. 3a in the opened state.

FIG. 3a shows in detail the front section of the pre-load unit P according to the invention. FIG. 3b shows the same front section in the opened state (without the upper leaf-like unit 3). The lens L is located in the chamber 14 between the leaf-like units 3. The leaf-like units 3 have boundaries 13a-13d around the chamber 14. These boundaries 13a-13d are wave-shaped and engage in each other with a meshing action. They are slightly raised and thus form a chamber 14 into which a lens L can be introduced.

Figure 4:
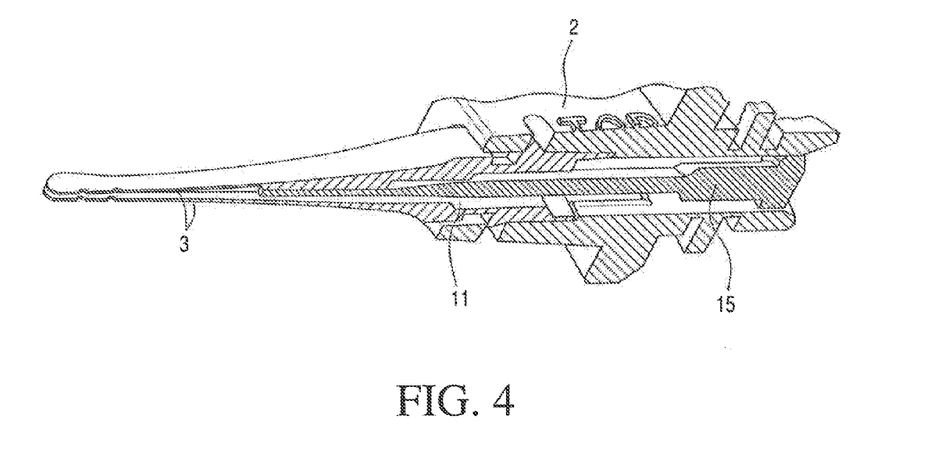
FIG. 4 shows a cross section through an embodiment of the pre-load unit according to the invention.

FIG. 4 shows a cross section through an embodiment of the pre-load unit P according to the invention. In its interior, the housing 2 has a continuous bore in which the lens-receiving part 11 is locked. A slide 15 is likewise arranged in the interior of the housing 2 and is freely movable there. The slide 15 tapers toward the front, such that it can be moved between the leaf-like units 3 as far as the chamber in which the lens L is located.

Figure 5:
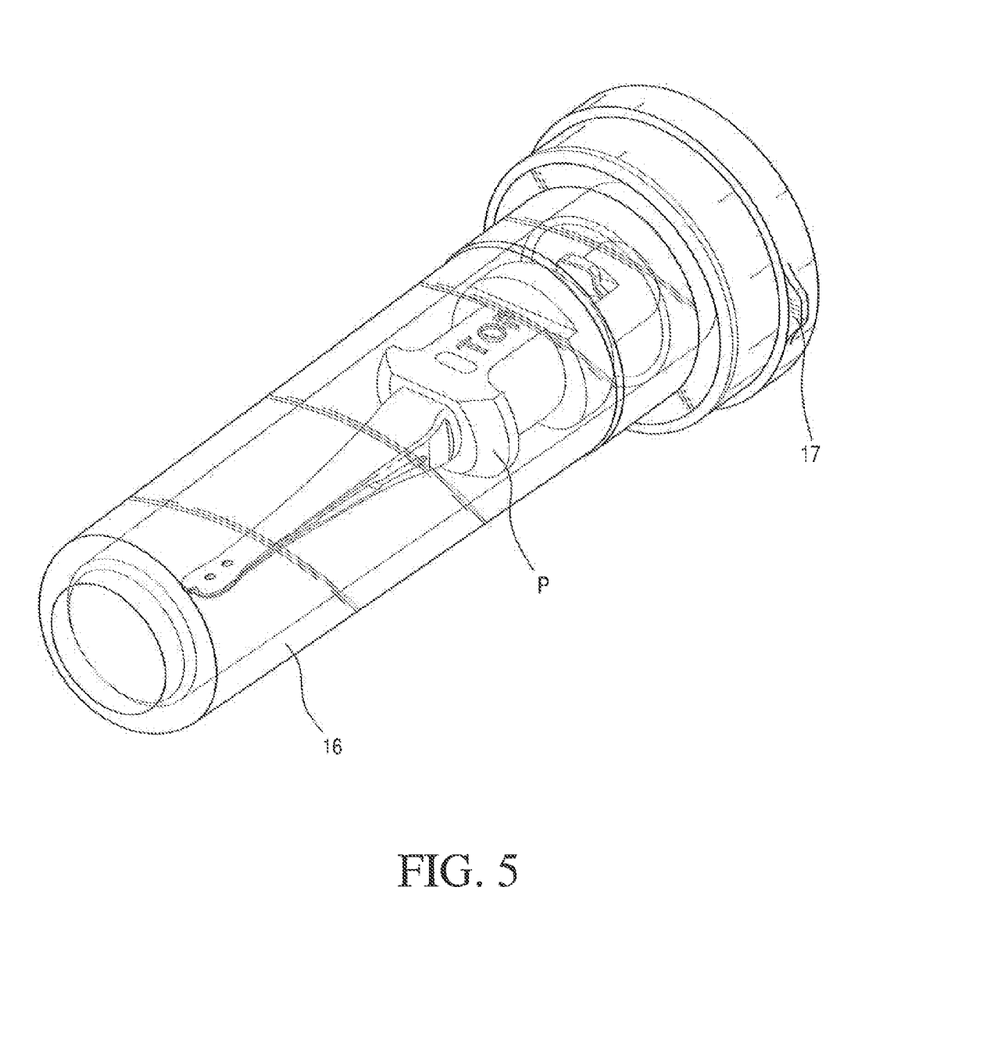
FIG. 5 shows an embodiment of the kit according to the invention composed of storage unit and pre-load unit.

FIG. 5 shows an embodiment of the kit according to the invention, which comprises a storage unit 16. In the interior of the storage unit 16, the pre-load unit P is stored in physiological saline. The storage unit 16 is made of glass. It is closed in a watertight manner with a stopper 17.

Figure 6:
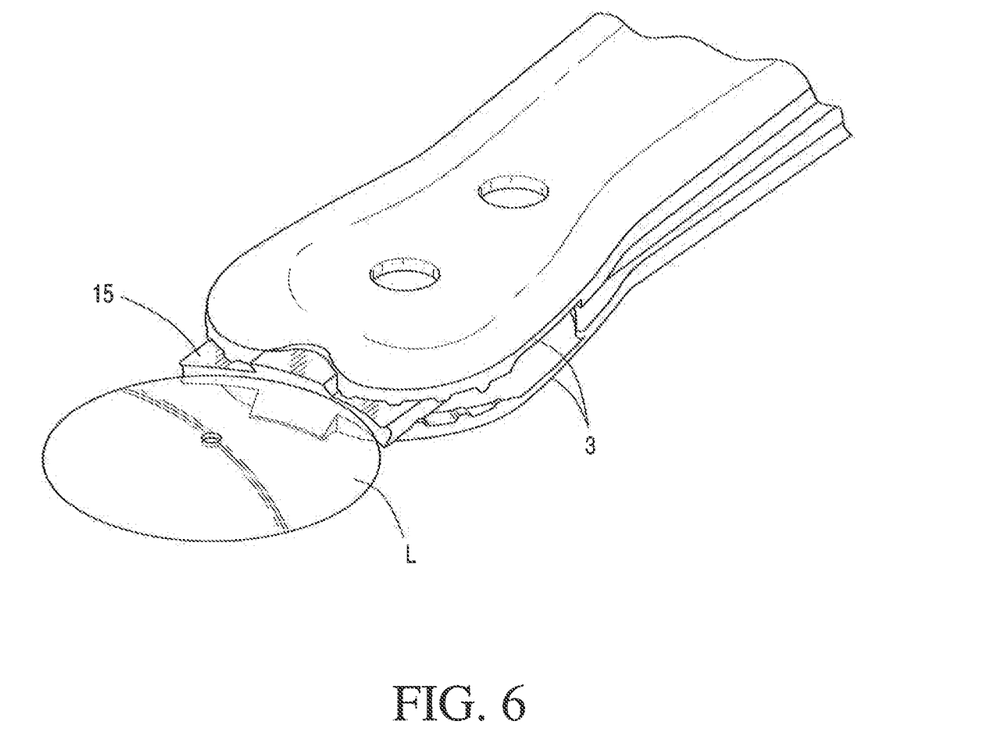
FIG. 6 shows the release of the lens from the pre-load unit according to the invention.

FIG. 6 shows how a lens L is released from the pre-load unit according to the invention. The slide 15 is pushed forward until it is in contact with the lens L. The leaf-like units 3 are thereby spread apart from each other. The leaf-like units 3 can now be drawn back by a defined distance, while the slide 15 holds the lens L at the previously oriented site. The lens L is then released, and the applicator according to the invention can be removed.

Figure 7:
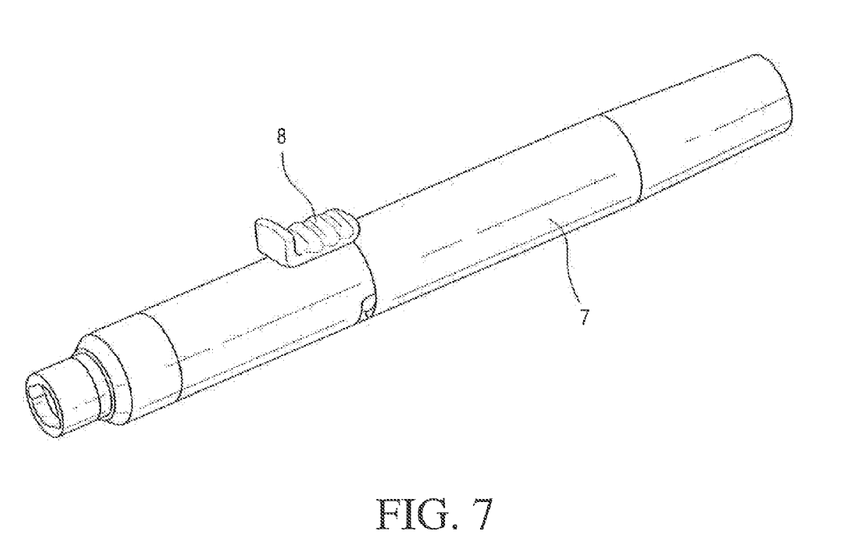
FIG. 7 shows an alternative embodiment of the grip piece according to the invention.

FIG. 7 shows an alternative embodiment of the grip piece 7 according to the invention. This grip piece has only one control element 8. The control element 8 is used to move the slide 15 (not shown here). The control element 8 is connected to corresponding insert parts (likewise not shown here) in the interior of the grip piece 7 by way of an elongate opening in the grip piece 7. These insert parts are akin to the ejector of a gun. If the control element 8 on the surface of the grip piece 7 is moved forward, the insert parts come into contact with the slide 15 of the pre-load unit P and move the slide 15 forward independently of the rest of the pre-load unit P. The maximum forward movement of the slide 15 by the control element 8 releases a locking mechanism (not shown), for example a pin, as a result of which the rest of the pre-load unit P, with the leaf-like units 3 arranged thereon, becomes movable. The release of the locking mechanism preferably brings about an automatic movement of the rest of the pre-load unit P, with the leaf-like units 3 arranged thereon, into the grip piece 7, for example via a spring mechanism. In this way, release of the lens is achieved through the maximum forward movement of the single control element 8.

The invention claimed is:

1. A pre-load unit (P) for inserting lenses into the eye of a human or animal, comprising
   i) a housing (2) adapted for fastening the unit to a grip piece (7) such that the housing and the grip piece can be dismantled into individual parts,
   ii) a lens-receiving part (11) arranged on or in the housing (2) and comprising a section that protrudes from the housing (2) and that has at least two separate leaf-like units (3) which, at least at their ends directed away from the housing (2), are in releasable contact with each other and there form a chamber (14) for storing an optical lens (L),
   iii) a slide (15), which is arranged movably in the interior of the housing (2) and can be moved between the leaf-like units (3) of the lens-receiving unit (11), wherein the pre-load unit and the grip piece can be connected to each other in such a way that the pre-load unit can be drawn back into the grip piece and the slide remains in position and a lens contained in the pre-load unit can be released from the pre-load unit.

2. The pre-load unit (P) as claimed in claim 1, wherein the two leaf-like units (3) each have a hole (4), which holes (4) are arranged such that they lie directly over each other and form an opening through the center of the chamber (14) for storing an optical lens (L).

3. The pre-load unit (P) as claimed in claim 1, wherein a boundary of the chamber for storing an optical lens (L) is formed at least partially by wave-shaped sections (13a-13d), which are present on both leaf-like units (3) and are arranged such that the sections of one leaf-like unit (3) mesh with the corresponding sections of the other leaf-like unit (3).

4. The pre-load unit (P) as claimed in claim 1, wherein at least one leaf-like unit (3) has a further hole (5), which is arranged above a boundary of the chamber (14) for storing an optical lens (L).

5. A kit comprising a storage unit (16) and a pre-load unit (P) as claimed in claim 1, in the interior of the storage unit (16), wherein the storage unit (16) is made of a watertight material and can be closed in a watertight manner with a stopper (17).

6. The kit as claimed in claim 5, wherein the interior of the storage unit (16) is filled with physiological saline solution.

7. The kit as claimed in claim 5, wherein the pre-load unit (P) is stored with an optical lens (L).

8. The kit as claimed in claim 5, wherein a grip piece (7) for connection to the pre-load unit (P) is additionally provided.

9. An applicator (1) comprising a pre-load unit (P) as claimed in claim 1 and a grip piece (7), wherein the pre-load unit (P) and the grip piece (7) are connected to each other in such a way that the pre-load unit (P) can be moved inside the grip piece (7).

10. The applicator (1) as claimed in claim 9, wherein control elements (8, 9) for moving the slide (15) and the rest of the pre-load unit (P) are provided on the grip piece (7).

11. The applicator (1) as claimed in claim 9, wherein a first control element (8) is provided for moving the slide (15) and a second control element (9) is provided for moving the rest of the pre-load unit (P), wherein the second control element (9) can only be operated when the first control element (8) is located in a position in which the slide (15) moved by it is driven out to the maximum extent from the housing of the pre-load unit (P).

12. The applicator (1) as claimed in claim 9, wherein a control element (8) for moving the slide (15) is provided on the grip piece (7).

13. The applicator as claimed in claim 9, wherein the pre-load unit (P) is fitted with an optical lens.

14. A method for inserting an optical lens (L) into the eye of a human or animal, comprising the steps of
   i) positioning an applicator (1) as claimed in claim 9 at the desired location of the eye, such that the center of the optical lens (L) contained in the applicator (1) lies on the visual axis of the eye;
   ii) pushing the slide forward by means of a first control element (8) on the grip piece (7), until the slide (15) comes into contact with the lens (L) without moving the latter, wherein at the same time the leaf-like units (3) of the lens-receiving part (11) are spread apart from each other;
   iii) withdrawing the rest of the pre-load unit (P) from the eye by a defined distance by means of a second control element (9) on the grip piece (7), with simultaneous fixing of the slide (15), as a result of which the lens (L) is released from the applicator (1).

15. The method as claimed in claim 14, wherein the positioning of the applicator (1) in step a) is achieved by the lens (L) being positioned by means of the holes (4), which are arranged in the leaf-like units (3) in such a way that the holes (4) lie directly over each other and form an opening through the center of the chamber (14) for storing an optical lens (L).

16. Method of use of a pre-load unit (P) as claimed in claim 1 or of an applicator (1) as claimed in claim 9, comprising the step of inserting an optical lens (L) into the eye of a human or animal with said pre-load unit or applicator.

17. Method of use of a pre-load unit (P) as claimed claim 1, comprising a step of inserting a donor cornea into the eye of a human or animal.

18. Method of using an applicator as claimed in claim 9, comprising a step of inserting a donor cornea into the eye of a human or animal.

* * * * *